US008343230B2

(12) United States Patent
Hanes

(10) Patent No.: US 8,343,230 B2
(45) Date of Patent: Jan. 1, 2013

(54) ORTHOPAEDIC BEARING MATERIAL

(75) Inventor: Mark D. Hanes, Winona Lake, IN (US)

(73) Assignee: DePuy Products, Inc., Warsaw, IN (US)

(*) Notice: Subject to any disclaimer, the term of this patent is extended or adjusted under 35 U.S.C. 154(b) by 1994 days.

(21) Appl. No.: 11/232,594

(22) Filed: Sep. 22, 2005

(65) Prior Publication Data
US 2007/0067044 A1 Mar. 22, 2007

(51) Int. Cl.
A61F 2/28 (2006.01)
F16C 33/00 (2006.01)
(52) U.S. Cl. ..................................... 623/23.58; 508/100
(58) Field of Classification Search .................. 508/100; 623/23.58
See application file for complete search history.

(56) References Cited

U.S. PATENT DOCUMENTS

| | | | |
|---|---|---|---|
| 3,297,805 A | 1/1967 | Rottig et al. | |
| 3,954,927 A | 5/1976 | Duling et al. | |
| 4,454,612 A | 6/1984 | McDaniel et al. | |
| 4,670,508 A | 6/1987 | Ohdaira et al. | |
| 4,778,601 A | 10/1988 | Lopatin et al. | |
| 4,880,843 A | 11/1989 | Stein | |
| 5,275,838 A | 1/1994 | Merrill | |
| 5,288,818 A | 2/1994 | Livingston, Jr. et al. | |
| 5,414,049 A | 5/1995 | Sun et al. | |
| 5,489,303 A | 2/1996 | Sasaki et al. | |
| 5,593,719 A | 1/1997 | Dearnaley et al. | |
| 5,594,055 A | 1/1997 | Young | |
| 5,721,334 A | 2/1998 | Burstein et al. | |
| 5,827,904 A | 10/1998 | Hahn | |
| 5,844,027 A | 12/1998 | Burdick et al. | |
| 5,879,400 A | 3/1999 | Merrill et al. | |
| 6,017,975 A | 1/2000 | Saum et al. | |
| 6,174,934 B1 | 1/2001 | Sun et al. | |
| 6,228,900 B1 | 5/2001 | Shen et al. | |
| 6,242,507 B1 | 6/2001 | Saum et al. | |
| 6,277,390 B1 | 8/2001 | Schaffner | |
| 6,281,264 B1 | 8/2001 | Salovey et al. | |
| 6,316,158 B1 | 11/2001 | Saum et al. | |
| 6,365,089 B1 | 4/2002 | Krebs et al. | |
| 6,379,741 B1 | 4/2002 | Komvopoulos et al. | |
| 6,395,799 B1 | 5/2002 | Johnson | |
| 6,448,315 B1 | 9/2002 | Lidgren et al. | |
| 6,494,917 B1 | 12/2002 | McKellop et al. | |
| 6,800,670 B2 | 10/2004 | Shen et al. | |
| 6,818,172 B2 | 11/2004 | King et al. | |
| 2002/0125614 A1 | 9/2002 | King et al. | |
| 2003/0083433 A1 | 5/2003 | James et al. | |
| 2003/0125513 A1 | 7/2003 | King | |
| 2003/0144741 A1 | 7/2003 | King et al. | |
| 2003/0144742 A1 | 7/2003 | King et al. | |
| 2003/0149125 A1 | 8/2003 | Muratoglu et al. | |
| 2003/0193110 A1 | 10/2003 | Yaritz et al. | |
| 2003/0212161 A1* | 11/2003 | McKellop et al. ................. 522/3 |
| 2004/0156879 A1 | 8/2004 | Muratoglu et al. | |
| 2004/0210316 A1 | 10/2004 | King et al. | |
| 2004/0262809 A1 | 12/2004 | Smith et al. | |
| 2004/0265165 A1 | 12/2004 | King | |
| 2004/0266903 A1 | 12/2004 | King | |
| 2005/0019366 A1 | 1/2005 | Zeldis | |
| 2005/0065307 A1 | 3/2005 | King et al. | |
| 2005/0069696 A1 | 3/2005 | King et al. | |
| 2006/0004168 A1 | 1/2006 | Greer et al. | |
| 2006/0142868 A1* | 6/2006 | Mimnaugh ................. 623/20.32 |
| 2006/0149387 A1 | 7/2006 | Smith et al. | |
| 2006/0149388 A1 | 7/2006 | Smith et al. | |

FOREIGN PATENT DOCUMENTS

| | | |
|---|---|---|
| DD | 227 328 A1 | 9/1985 |
| EP | 0 047 171 A2 | 3/1982 |
| EP | 0 335 613 A2 | 10/1989 |
| EP | 0 730 001 A1 | 9/1996 |
| EP | 0 805 178 A1 | 11/1997 |
| EP | 1 086 709 A1 | 3/2001 |
| EP | 1 493 775 A1 | 1/2005 |
| EP | 1 779 876 A3 | 5/2007 |
| JP | 48-054168 A | 7/1973 |
| JP | 60-252645 A | 12/1985 |
| WO | WO 85/04365 A1 | 10/1985 |
| WO | WO 86/02656 A1 | 5/1986 |
| WO | WO 93/25247 A1 | 12/1993 |
| WO | WO 97/29895 A1 | 8/1997 |
| WO | WO 00/49079 A1 | 8/2000 |
| WO | WO 02/26464 A1 | 4/2002 |
| WO | WO 03/057769 A1 | 7/2003 |
| WO | WO 03/087217 A1 | 10/2003 |
| WO | WO 2004/064618 A | 8/2004 |

OTHER PUBLICATIONS

U.S. Appl. No. 11/021,680, filed Dec. 23, 2004, King et al.
U.S. Appl. No. 11/241,136, filed Sep. 30, 2005, King et al.
Barr et al., "EPR as a quality control method for the release of cross-linked ultra high molecular weight polyethylene," Bruker EPR Application Note, 1-3 (Bruker Instruments, Inc., Billerica, Massachusetts, Feb. 28, 2003).
Bavaresco et al., "Devices for use as an artificial articular surface in joint prostheses or in the repair of osteochondral defects," Artificial Organs, 24 (3): 202-205 (2000).
Beauregard et al., "Synthesis and characterization of a novel UHMWPE interpenetrating polymer network," Biomedical Sciences Instrumentation, 35: 415-419 (Apr. 16, 1999).
European Patent Office, Search Report in European Patent Application No. 06255075.1 (Mar. 30, 2007).

(Continued)

Primary Examiner — Jim Goloboy

(57) ABSTRACT

Disclosed is a polymeric orthopaedic bearing material for use as an implant material or part thereof comprising one or more crosslinked regions and one or more non-crosslinked or substantially non-crosslinked regions at the surface. The bearing material can be prepared from a crosslinkable polymer, e.g., ultrahigh molecular weight polyethylene. The orthopaedic bearing material has an advantageous combination of at least one wear property and at least one mechanical property. Also disclosed are processes for producing orthopaedic bearing materials, for example, by irradiating a raw material in consolidated form through a radiation mask having a perforated pattern for crosslinking selected regions of the raw material, and optionally shaping the raw material into a bearing material. Alternatively, a pulsed radiation beam can be used for crosslinking.

29 Claims, No Drawings

OTHER PUBLICATIONS

King et al., "Hydrophilic, pourous ultra-high molecular weight polyethylene for orthopaedic implants," *Transactions 7th World Biomaterials Congress*, 1909 (May 2004).

Kurtz et al., "Advanced in the processing, sterilization, and crosslinking of ultra-high molecular weight polyethylene for total joint arthroplasty," *Biomaterials*, 20 (18): 1659-1688 (1999).

Oral et al., "α-Tocopherol-doped irradiated UHMWPE for high fatigue resistance and low wear," *Biomaterials*, 25 (24): 5515-5522 (2004).

Shutov et al., "Cellular UHMW polyethylene produced by non-foaming leaching technique: Morphology and properties," *J. Cell. Plast.*, 38: 163-176 (Mar. 2002).

Stein, "Ultra high molecular weight polyethylene (UHMWPE)", *Engineered Materials Handbook vol. 2: Engineering Plastics*, 167-171 (ASM International, Materials park, Ohio, US, 1998).

Veiga-Crespo et al., "Influence of culture conditions of *Gordonia jacobaea* MV-26 on canthaxanthin production," *Int. Microbiol.*, 8 (1): 55-58 (Mar. 2005).

Zhang et al., "Surface modification of UHMWPE for use in total joint replacements," *Biomedical Science Instrumentation*, 40: 13-17 (Apr. 2004).

\* cited by examiner

ORTHOPAEDIC BEARING MATERIAL

BACKGROUND OF THE INVENTION

The invention relates in general to a polymeric orthopaedic bearing material for use as an implant or an implant part, and in particular to an orthopaedic bearing material made of ultra-high molecular weight polyethylene (UHMWPE). The bearing material has an advantageous combination of wear or abrasion resistance and toughness.

Implants have been used to replace parts of the human body, e.g., the hip, the knee, and the extremity joints. In an implant, the bearing material having a bearing surface is paired with an opposing metal or ceramic component. Polymeric materials, for example, UHMWPE, have been used for producing bearing materials. The high molecular weight of the polymer imparts certain desirable characteristics such as high impact strength and abrasion resistance. However, the bearing material, even when made of UHMWPE, wears due to use over time and, as a result, introduces debris, e.g., microscopic wear particles, into the surrounding tissues. The body's reactions to the debris can involve inflammation and deterioration of the affected tissues. In particular, the bone to which the prosthesis or implant is anchored can deteriorate and become inflamed. Eventually, the prosthesis may become painfully loose in which case it must be replaced. It is generally accepted by orthopaedic surgeons and biomaterials scientists that the reaction of the affected tissue to wear debris is one of the major causes of long-term failure of such prostheses.

Crosslinking of the polymer, e.g., by the use of ionizing radiation such as gamma radiation or e-beam or of plasma gases, has been proposed for improving the wear resistance of implants. While crosslinking improves the wear resistance, it also tends to lower one or more of the desirable mechanical properties. In particular, crosslinking tends to lower the toughness of the bearing material resulting in a greater susceptibility to mechanical failure of the implant. Crosslinking, for example, by irradiation, can also change the color of the bearing material. It is believed that the change in color and/or mechanical properties may be due to oxidation of the polymer chains leading to a decrease in polymer molecular weight. The ionizing radiation breaks molecular bonds, resulting in polymer chain scission, and creates free radicals that are highly reactive species. With the passage of time, the severed chains can recombine, crosslink with adjacent chains, or combine with other species such as oxygen. In the presence of oxygen, the severed chain is also likely to form an oxygenated species which is then not able to form crosslinks or recombine, resulting in a reduction of molecular weight. It is believed that the reduction in molecular weight causes a reduction in one or more mechanical properties, e.g., toughness, impact strength, or tensile strength, and can in severe cases cause embrittlement.

Further, some of the free radicals formed during irradiation are not capable of reacting in a short time frame due to their remote location within the polymer structure and thus can exist as isolated free radicals for long periods of time. These isolated free radicals are therefore difficult to neutralize during the manufacture of the bearing material. However, even these free radicals eventually react as a result of migration of oxygen or other reactive species to such remote locations over time, which can also lead to time-dependent degradation of the properties.

Approaches have been pursued to stabilize or neutralize the free radicals. For example, in one approach, the use of vitamin E has been proposed to stabilize the free radicals. Thus, a vitamin E-treated UHMWPE bearing material is irradiated to obtain a crosslinked bearing material. A disadvantage of this approach is that the entire bearing material, i.e., the surface and the body, is irradiated. As a result, some of the mechanical properties of the bearing material are compromised. In addition, the presence of vitamin E in an irradiated polymer can impart a strong yellow-brown color to the material which is aesthetically undesirable.

In another approach, it has been proposed to crosslink the entire articular surface of the bearing material. Since the crosslinked surface layer has reduced impact strength, a disadvantage of this approach is that the crosslinked surface layer could be damaged or worn through relatively easily, thereby exposing the underlying polymer which has a poor wear resistance. In addition, the surface layer can act as an initiation point for other mechanical failures.

In yet another approach, UHMWPE powder is irradiated to obtain a crosslinked powder, which is then blended with non-crosslinked UHMWPE powder, and the resulting blend is molded into a bearing material. This approach produces a bearing material, which contains throughout its thickness, discrete crosslinked polymer domains or particles surrounded by a non-crosslinked matrix. A disadvantage of this approach is that it can be difficult to obtain good adhesion between the crosslinked particles or domains and the non-crosslinked particles or matrix. If the proportion of the crosslinked powder is increased to obtain improvement in wear resistance, some of the mechanical properties of the resulting bearing material could become poor.

The foregoing shows that there exists a need for bearing materials having an advantageous combination of at least one wear property and at least one mechanical property. The invention provides such a bearing material.

BRIEF SUMMARY OF THE INVENTION

The invention provides an orthopaedic bearing material for use as an implant or part thereof, comprising one or more crosslinked regions and one or more non-crosslinked or substantially non-crosslinked regions at the bearing surface. The invention provides an orthopaedic bearing material comprising one or more irradiated regions and one or more non-irradiated or substantially non-irradiated regions at the surface. The bearing material may be crosslinked, non-crosslinked, or substantially non-crosslinked below the surface in the thickness direction. The invention also provides orthopaedic implants comprising the orthopaedic bearing material.

The invention further provides processes for producing the orthopaedic bearing material. In one aspect, the bearing material can be prepared by a process involving irradiating a raw material in consolidated form (e.g., consolidated powder) of the bearing material through an irradiation mask having a perforation or a perforated pattern for allowing radiation only to a selected region or selected regions of the raw material. In another aspect, a pulsed radiation beam can be used to produce a partially irradiated surface. Thus, a raw material in consolidated form of the bearing material comprising a crosslinkable polymer and/or the radiation beam can be moved relative to each other, to create irradiated and non-irradiated or substantially non-irradiated regions, or crosslinked and non-crosslinked or substantially non-crosslinked regions. The irradiated raw material may be further processed to obtain a bearing material.

The orthopaedic bearing material of the invention has an advantageous combination of at least one wear property, e.g., wear resistance, and at least one mechanical property, e.g., toughness. The invention provides one or more advantages, for example, it allows the irradiation of polymers to a high dose while preserving one or more of the desirable mechanical properties such as toughness, Young's modulus, impact strength, fatigue strength, yield stress, tensile strength at break, and elongation at break. The invention provides for a method to independently control the level of crosslinking and at least one mechanical property of the polymer, and/or the invention provides for a method to quench free radicals without remelting the whole component. The crosslinked regions provide improved wear properties, and the non-crosslinked or substantially non-crosslinked regions provide improved mechanical properties, e.g., toughness or reduced embrittlement. Since a significant portion of the bearing material is not irradiated, it is possible to use a much higher radiation dose to create crosslinked regions, without significantly sacrificing one or more of the desirable mechanical properties, than would be typically possible if the entire bearing material (surface and body) were to be irradiated.

DETAILED DESCRIPTION OF THE INVENTION

The invention is predicated on the concept that a desirable combination of wear resistance and a high mechanical property can be realized if the orthopaedic bearing material comprises one or more crosslinked regions and one or more non-crosslinked or substantially non-crosslinked regions at the articular surface, i.e., the surface of the bearing material that comes in contact with an opposing metal or ceramic component. The crosslinked regions provide improved wear resistance, and the non-crosslinked or substantially non-crosslinked regions provide or retain advantageous mechanical properties.

Accordingly, in an embodiment, the invention provides an orthopaedic bearing material suitable for a medical implant or medical implant part, the bearing material comprising a body and a bearing surface, the bearing surface comprising one or more crosslinked regions of a polymer and one or more non-crosslinked or substantially non-crosslinked regions of a polymer. The body may contain both crosslinked and non-crosslinked regions.

The crosslinked regions in accordance with the invention are macroscopic regions. These regions include a collection of crosslink bonds as well as non-crosslinked polymer chain segments that lie between the crosslink bonds. Each of the crosslinked regions, in accordance with the invention, can have any suitable shape, e.g., a cylindrical or cone shape. This shape will have an aspect ratio greater than 1, preferably greater than 5, and more preferably greater than 10. Crosslinked powders in the art, in contrast, will have crosslinked regions with an aspect ratio of approximately 1.0.

Each of the crosslinked regions of the invention can have the same area or different area. Each of the non-crosslinked regions can have the same area or different area. Each of the crosslinked regions can have the same area or different area as each of the non-crosslinked regions. The crosslinking region can be present in one, two, or all three dimensions of the bearing material. Crosslinked regions may or may not intersect with other crosslinked regions.

Any suitable crosslinkable polymer can be used to prepare the bearing material, particularly a radiation-crosslinkable polymer, such as a polyolefin, for example, polyethylene. The crosslinkable polymer can be a homopolymer, copolymer, or a combination thereof. For use as implants, the polymer desirably has good wear resistance, advantageous mechanical properties, biocompatibility, and chemical resistance.

The crosslinkable polymer generally possesses a weight average molecular weight of about $10^5$ atomic mass units (amu) or more. Typically, the weight average molecular weight of the polymer, e.g., polyethylene, is generally between about $4 \times 10^5$ to about $10^7$ amu. The polymer preferably is an ultrahigh molecular weight polyethylene (UHMWPE). As utilized herein, the term "ultrahigh molecular weight polyethylene" refers to a polyethylene polymer having a weight average molecular weight of about 400,000 amu or more. Preferably, the UHMWPE has a weight average molecular weight of about 1,000,000 (e.g., about 2,000,000 or about 3,000,000) amu or more. Typically, the weight average molecular weight of the UHMWPE is about 10,000,000 amu or less, more preferably about 6,000,000 amu or less. UHMWPE suitable for use in the invention includes, but is not limited to, commercially available UHMWPE's such as GUR 1050 and GUR 1020 powdered UHMWPE (weight average molecular weight of about 2,000,000 to about 6,000,000 amu) from Ticona (Summit, N.J.).

Any suitable fraction of the orthopaedic bearing material surface can be crosslinked or non-crosslinked. In one embodiment, at least 10% or more of the bearing material surface area is non-crosslinked, for example, from about 10% to about 90% of the bearing material surface area is non-crosslinked. In other embodiments, from about 25% to about 75% of the bearing material surface area is non-crosslinked, and in yet other embodiments, from about 40% to about 60% of the bearing material surface area is non-crosslinked.

The orthopaedic bearing material of the invention can have any suitable thickness. In an embodiment where the bearing material is used as a liner of an implant, the thickness can be about 3 mm or more, for example, from about 3 mm to about 30 mm. In some embodiments, the thickness is from about 6 mm to about 28 mm, and in other embodiments, the thickness is from about 8 mm to about mm. If the orthopaedic bearing material itself is used as an implant, the thickness can be about 3 mm or more, for example, from about 3 mm to about 30 mm. In some embodiments, the thickness is from about 6 mm to about 28 mm, and in other embodiments, the thickness is from about 8 mm to about 25 mm.

The crosslinked region of the orthopaedic bearing material surface can extend to any suitable thickness or depth, for example, to a thickness of about 100% or less, such as a thickness of from about 98% to about 20%, in some embodiments to a thickness of from about 95% to about 25%, and in other embodiments to a thickness of from about 90% to about 30%, of the thickness of the bearing material is crosslinked. In one embodiment, the interior of the bearing material is not crosslinked or substantially not-crosslinked. In another embodiment, the crosslinked region extends through part, all, or substantially all of the thickness of the bearing material.

The crosslinked regions of the bearing material surface can be of any suitable size and shape. For example, the crosslinked region can be, for example, circular, square, elliptical, trilobal, multilobal, triangular, tetragonal, rectangular, trapezoidal, pentagonal, hexagonal, heptagonal, octagonal, sector of a circle, quadrant, segment of a circle, sextant, annulus, oblong, or of other shapes, or shaped like a star, cross, crescent, or other objects. One or more of the crosslinked regions can be connected to one another.

The crosslinked regions of the bearing material of the invention can be disposed at any suitable angle with respect to one another. For example, one crosslinked region can be disposed at an angle of from about 10 degrees to about 170 degrees, in some embodiments, from about 45 to about 135 degrees, and in other embodiments from about 80 to about 100 degrees, with respect to another crosslinked region.

The invention further provides a medical implant or medical implant part comprising the orthopaedic bearing material. Thus, the orthopaedic bearing material itself can be an implant, or it can be part of an implant. The orthopaedic bearing material can be used in combination with another component, e.g., metal, composite, or plastic component, to constitute an implant.

It is contemplated that the bearing material of the invention can have a number of uses. For example, the bearing material can be a prosthetic acetabular cup, an insert or liner of the acetabular cup, a trunnion bearing or a component thereof, a prosthetic tibial plateau, a patellar button, a prosthetic talar surface, a prosthetic radio-humeral joint, an ulno-humeral joint, a glenoro-humeral articulation, an intervertebral disk replacement, a facet joint replacement, a temporo-mandibular joint, or a finger joint. The bearing material can be a liner for the acetabular component of a hip arthroplasty or the tibial bearing for a knee arthroplasty.

The orthopaedic bearing material or implant of the invention, can find use as a prosthesis for any suitable part of the body, e.g., such as a component of a joint in the body. For example, in a hip joint, the orthopaedic bearing material or implant can be a prosthetic acetabular cup, or the insert or liner of the cup, or a component of a trunnion bearing (e.g., between the modular head and the stem). In a knee joint, the orthopaedic bearing material or implant can be a prosthetic tibial plateau (femoro-tibial articulation), a patellar button (patello-femoral articulation), a trunnion or other bearing component, depending on the design of the artificial knee joint. For example, in a knee joint of the meniscal bearing type, both the upper and lower surfaces of the orthopaedic bearing material or implant, i.e., those surfaces that articulate against metallic or ceramic surfaces, may be surface-crosslinked. In an ankle joint, the orthopaedic bearing material or implant can be the prosthetic talar surface (tibio-talar articulation) or other bearing component. In an elbow joint, the orthopaedic bearing material or implant can be the prosthetic radio-humeral joint, the ulno-humeral joint, or other bearing component. In a shoulder joint, the orthopaedic bearing material or implant can be used in the glenoro-humeral articulation. In the spine, the orthopaedic bearing material or implant can be used in intervertebral disk replacement or facet joint replacement. The orthopaedic bearing material or implant can also be made into a temporo-mandibular joint (jaw) or a finger joint. The orthopaedic bearing material can find use as an implant in any part of a body, such as the hip, knee, and extremities.

The orthopaedic bearing material of the invention can be produced by any suitable method. For example, a raw material in consolidated form of the bearing material can be first prepared, and the crosslinked regions can be created subsequently. The raw material in consolidated form is a precursor to the bearing material, which can be of any consolidated shape, e.g., a rod, sheet, preform, or a finished part. The raw material can be prepared by any suitable method, for example, by molding, extrusion, or solvent casting. Alternatively, the raw material in consolidated form can be machined or molded from a block or sheet of a crosslinkable polymer.

The crosslinked regions can be created by any suitable method, for example, by irradiation. The invention provides a process for producing a bearing material for a medical implant or medical implant part, in which the process comprises (a) providing a raw material in consolidated form comprising a radiation-crosslinkable polymer, the raw material in consolidated form having a surface, i.e., a surface which would become the articulating surface in an implant, (b) applying an irradiation mask to at least a portion of the surface of the raw material in consolidated form, and (c) irradiating the raw material in consolidated form to crosslink at least a portion of the polymer that is not protected by the irradiation mask, optionally shaping the raw material into a bearing material for a medical implant or medical implant part, to produce a bearing material comprising one or more crosslinked regions and one or more non-crosslinked or substantially non-crosslinked regions at the surface. If the raw material is an unfinished product, e.g., rod, sheet, or preform, then the irradiated raw material can be further processed, e.g., by machining, to produce the bearing material.

The irradiation mask can be of any suitable configuration. The irradiation mask desirably contains at least one perforation, for example, from about 1 to about 10,000 perforations, or from about 20 to about 1000 perforations, to permit irradiation of the polymer through the perforation. The perforation can be of any suitable shape. For example, the perforation can be, for example, circular, square, elliptical, triangular, trilobal, multilobal, tetragonal, rectangular, trapezoidal, pentagonal, hexagonal, heptagonal, octagonal, sector of a circle, quadrant, segment of a circle, sextant, annulus, oblong, or other shapes. In addition, the perforation can be a slit, or shaped like an object such as a star, cross, crescent, or other objects. One or more of the perforations can be connected to each other. Any suitable combination of perforations, which can be connected or disconnected, can be employed. While the shape of the crosslinked regions can be the same or substantially the same as the shape of the perforations in the mask, crosslinking can also occur in a region immediately surrounding the irradiated region. Thus, the size of the crosslinked region can be the same or larger than the size of the perforation.

The perforation can be of any suitable size, for example, about $0.0001$ mm$^2$ or more, e.g., from about $0.001$ mm$^2$ to about $10$ mm$^2$, or from about $0.01$ mm$^2$ to about $1$ mm$^2$. The radiation and the mask can be applied in one or multiple dimensions.

The irradiation mask, which should substantially block or absorb the radiation of interest, can be made of any suitable material which has high shielding potential for ionizing radiation, for example, a metal, ceramic, composite, or any combination thereof. One or more than one mask can be used, for example, a stack of two, three, four, or more masks can be employed if desired to obtain a desired degree and/or depth of crosslinking.

The perforations can be positioned in the irradiation mask with respect to each other at any suitable angle. Such positioning allows for the preparation of orthopaedic bearing materials having crosslinked regions disposed at a desired angle with respect to each other. Thus, for example, the raw material in consolidated form can be irradiated to produce at least a first crosslinked region and a second crosslinked region, the second crosslinked region being disposed at any suitable angle, for example, an angle of from about 10 to about 170 degrees, such as, e.g., in certain embodiments, from about 45 to about 135 degrees and in other embodiments, an angle of about 80 to about 100 degrees relative to the first crosslinked region.

Irradiation can be carried out by using any suitable radiation, e.g., ionizing radiation. Ionizing radiation is a radiation, in which an individual particle, e.g., electron, positron, alpha particle, or neutron, carries high enough energy, or an electromagnetic radiation having a high enough energy, to ionize an atom or molecule in the irradiated substrate. Examples of electromagnetic radiation include gamma radiation, X-ray, and ultraviolet light. A preferred radiation is electron beam (or e-beam), which has the advantage that it allows high dose rates, and is believed to result in less oxidation of the irradiated material than slower radiation sources such as gamma radiation. The e-beam can have any suitable amount of energy, such as 10 Mev or less, e.g., from about 1 Mev to about 20 Mev, of energy. Plasma treatment or crosslinking by gases such as acetylene and CTFE may be used in conjunction with irradiation. The e-beam can be continuous. Examples of continuous e-beam generators are Dynamatron and Rotatron.

The raw material in consolidated form can be exposed to any suitable amount or dose of radiation, e.g., about 2.5 Mrad or more of radiation, such as from about 3 to about 100 Mrad, or from about 5 to about 25 Mrad. The energy of the radiation, e.g., e-beam, is selected so that it is effective to crosslink at least a portion of the exposed surface of the raw material in consolidated form of the bearing material. With e-beam crosslinking, it can be advantageous to limit or eliminate ambient oxygen during irradiation. In that respect, an inert gas, e.g., nitrogen or argon, atmosphere can be provided to exclude ambient oxygen. Vacuum also can be used to exclude oxygen. The use of e-beam at high doses can produce localized melting of the polymer, resulting in quenching of free radicals while leaving the non-irradiated portions of the polymer below its melting point. Such an approach can lead to the production of a bearing material having an advantageous combination of at least one wear property and at least one mechanical property.

After the irradiation, optionally, the raw material in consolidated form, e.g., rod, sheet, or preform, can be shaped by suitable method, e.g., machining, a shape and size desired for the bearing material. The orthopaedic bearing material can be sterilized by a suitable method, e.g., by a non-irradiative method such as the use of ethylene oxide gas. The irradiation mask can be removed before or after sterilization. Optionally, the orthopaedic bearing material (or implant) thus produced can be further processed to eliminate or reduce any residual free radicals by any suitable method, for example, by annealing or remelting the irradiated material or by exposing the orthopaedic bearing material or implant to pressurized hydrogen or by ethylene oxide treatment. Alternatively, or in addition, the orthopaedic bearing material or implant can be exposed to a suitable antioxidant to stabilize any residual free radicals.

The invention also provides a process for producing an orthopaedic bearing material comprising one or more crosslinked regions and one or more non-crosslinked or substantially non-crosslinked regions at the surface, for a medical implant or medical implant part, the process comprising (a) providing a raw material in consolidated form of the bearing material, the raw material in consolidated form comprising a radiation-crosslinkable polymer, (b) providing a pulsed radiation beam, and (c) moving the raw material in consolidated form relative to the pulsed radiation beam, the pulsed radiation beam relative to the raw material in consolidated form, or both the raw material in consolidated form and the radiation beam, so that the pulsed radiation beam contacts at least a portion of the raw material in consolidated form, optionally shaping the raw material into a bearing material for a medical implant or medical implant part, whereby a bearing material having one or more crosslinked regions and one or more non-crosslinked or substantially non-crosslinked regions at the surface is produced.

The pulsed radiation beam can be any suitable radiation beam that is pulsed, e.g., e-beam. The raw material in consolidated form can be placed on any suitable carrier, such as a conveyor belt, platen, or stage that can assist in the placement of the raw material in consolidated form in the beam path. The carrier can be moved or programmed so as to allow desired regions of the raw material in consolidated form to be irradiated or crosslinked while leaving other regions non-irradiated or non-crosslinked. Thus, the raw material in consolidated form can be irradiated in a desired pattern.

The invention further provides a process for producing an orthopaedic bearing material for a medical implant or medical implant part, the process comprising (a) providing a raw material in consolidated form comprising a radiation-crosslinkable polymer, the raw material in consolidated form having a surface (b) providing a radiation source adapted to produce a pulsed radiation beam, (c) providing a carrier to carry the raw material in consolidated form and selectively move the raw material in consolidated form relative to the pulsed radiation beam, (d) placing the raw material in consolidated form on the carrier, (e) moving the carrier so that the pulsed radiation beam will contact a portion of the raw material in consolidated form that is to be irradiated, (f) activating the pulsed radiation beam to irradiate the portion of the raw material in consolidated form and crosslink at least a portion of the polymer contacted by the radiation beam, and (g) repeating steps (e) and (f) until the desired portions of the raw material in consolidated form have been irradiated, optionally shaping the raw material into a bearing material for a medical implant or medical implant part, to produce a bearing material comprising one or more crosslinked regions at the surface and one or more non-crosslinked or substantially non-crosslinked regions at the surface.

The radiation can be pulsed at any suitable rate, for example, from about 1 to about 1000 pulses per second, in some embodiments, from about 5 to about 500 pulses per second, and in other embodiments, from about 10 to about 300 pulses per second. An example of a pulsed e-beam source is an L-band accelerator.

If desired, in an embodiment, a mask can be placed on the raw material in consolidated form and a pulsed radiation can be used to irradiate and crosslink the polymer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. It is expected that skilled artisans could employ such variations as appropriate, and it is intended that the invention could be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An orthopaedic bearing material for a medical implant or medical implant part, the bearing material comprising a body and an articular bearing surface, the articular bearing surface comprising twenty or more crosslinked regions of a polymer wherein each of the twenty or more crosslinked regions of a polymer is separated from one another by one or more non-crosslinked or substantially non-crosslinked regions of a polymer.

2. The orthopaedic bearing material of claim 1, wherein the polymer is a radiation-crosslinkable polymer.

3. The orthopaedic bearing material of claim 2, wherein the radiation-crosslinkable polymer is a polyolefin.

4. The orthopaedic bearing material of claim 3, wherein the polyolefin is polyethylene.

5. The orthopaedic bearing material of claim 4, wherein the polyethylene is an ultrahigh molecular weight polyethylene having a weight average molecular weight of about 400,000 amu or more.

6. The orthopaedic bearing material of claim 5, wherein the ultrahigh molecular weight polyethylene has a weight average molecular weight of about 1,000,000 amu or more.

7. The orthopaedic bearing material of claim 1, wherein the body has a thickness, and one or more of the crosslinked regions extend through part or all of the thickness.

8. The orthopaedic bearing material of claim 1, wherein the articular bearing surface includes at least a first regularly shaped crosslinked region and a second regularly shaped crosslinked region, the second regularly shaped crosslinked region being disposed at an angle of about 45 to about 135 degrees relative to the first regularly shaped crosslinked region.

9. A medical implant comprising the orthopaedic bearing material of claim 1.

10. A medical implant comprising the orthopaedic bearing material of claim 2.

11. A medical implant comprising the orthopaedic bearing material of claim 3.

12. The medical implant of claim 9, which is selected from the group consisting of a prosthetic acetabular cup, an insert or liner of the acetabular cup, a trunnion bearing or a component thereof, a prosthetic tibial plateau, a patellar button, a prosthetic talar surface, a prosthetic radio-humeral joint, an ulno-humeral joint, a glenoro-humeral articulation, an intervertebral disk replacement, a facet joint replacement, a temporo-mandibular joint, and a finger joint.

13. The medical implant of claim 9, wherein the orthopaedic bearing material is a liner for an acetabular component of a hip arthroplasty or a tibial bearing for a knee arthroplasty.

14. A process for producing an orthopaedic bearing material for a medical implant or medical implant part, according to claim 1, the process comprising:
(a) providing a raw material in consolidated form comprising a radiation-crosslinkable polymer, the raw material in consolidated form having a surface,
(b) applying an irradiation mask to at least a portion of the surface of the raw material, and
(c) irradiating the raw material to crosslink at least a portion of the surface that is not protected by the irradiation mask, optionally shaping the raw material into a bearing material for a medical implant or medical implant part, to produce a bearing material comprising twenty or more crosslinked regions of a polymer wherein each of the twenty or more crosslinked regions of a polymer is separated from one another by one or more non-crosslinked or substantially non-crosslinked regions of a polymer at the surface.

15. The process of claim 14, wherein the radiation-crosslinkable polymer is a polyolefin.

16. The process of claim 15, wherein the polyolefin is polyethylene.

17. The process of claim 16, wherein the polyethylene is an ultrahigh molecular weight polyethylene having a weight average molecular weight of 400,000 amu or more.

18. The process of claim 17, wherein the raw material is irradiated by electron beam.

19. The process of claim 14, wherein the raw material in consolidated form is irradiated to produce at least a first crosslinked region and a second crosslinked region, the second crosslinked region being disposed at an angle of about 45 to about 135 degrees relative to the first crosslinked region.

20. The process of claim 14, wherein the raw material in consolidated form is a rod, a sheet, a preform, or a finished part.

21. A process for producing an orthopaedic bearing material having a body, a surface, and one or more crosslinked regions and one or more non-crosslinked or substantially non-crosslinked regions at the surface, for a medical implant or medical implant part, according to claim 1, the process comprising:
(a) providing a raw material in consolidated form of the bearing material, the raw material in consolidated form comprising a radiation-crosslinkable polymer,
(b) providing a pulsed radiation beam, and
(c) moving the raw material relative to the pulsed radiation beam, the pulsed radiation beam relative to the raw material, or both the raw material and the radiation beam, so that the pulsed radiation beam contacts at least a portion of the raw material, optionally shaping the raw material into a bearing material for a medical implant or medical implant part,
whereby a bearing material comprising twenty or more crosslinked regions of a polymer wherein each of the twenty or more crosslinked regions of a polymer is separated from one another by one or more non-crosslinked or substantially non-crosslinked regions of a polymer at the surface is produced.

22. The process of claim 21, wherein the radiation-crosslinkable polymer is a polyolefin.

23. The process of claim 22, wherein the polyolefin is polyethylene.

24. The process of claim 23, wherein the polyethylene is an ultrahigh molecular weight polyethylene having a weight average molecular weight of about 400,000 amu or more.

25. The process of claim 21, wherein the pulsed radiation beam is electron beam.

26. The process of claim 22, wherein the raw material in consolidated form is a rod, a sheet, a preform, or a finished part.

27. A process for producing an orthopaedic bearing material for a medical implant or medical implant part, according to claim 1, the process comprising:

(a) providing a raw material in consolidated form comprising a radiation-crosslinkable polymer, the raw material in consolidated form having a surface,
(b) providing a radiation source adapted to produce a pulsed radiation beam,
(c) providing a carrier to carry the raw material and selectively move the raw material relative to the pulsed radiation beam,
(d) placing the raw material on the carrier,
(e) moving the carrier so that the pulsed radiation beam will contact a portion of the raw material that is to be irradiated,
(f) activating the pulsed radiation beam to irradiate the portion of the raw material and crosslink at least a portion of the raw material contacted by the radiation beam, and
(g) repeating steps (e) and (f) until the desired portions of the raw material have been irradiated, optionally shaping the raw material into a bearing material for a medical implant or medical implant part, to produce a bearing material comprising twenty or more crosslinked regions of a polymer wherein each of the twenty or more crosslinked regions of a polymer is separated from one another by one or more non-crosslinked or substantially non-crosslinked regions of a polymer at the surface.

28. The process of claim 27, wherein the raw material in consolidated form is a rod, a sheet, a preform, or a finished part.

29. The orthopaedic bearing material of claim 1, wherein the articular bearing surface comprises twenty to 1000 crosslinked regions of a polymer.

* * * * *